United States Patent [19]

Straschewski

[11] Patent Number: 4,818,267

[45] Date of Patent: Apr. 4, 1989

[54] APPARATUS FOR WITHDRAWING A SAMPLE FROM A GLASS MELTING FURNACE

[75] Inventor: Helmut Straschewski, Kehl-Querbach, Fed. Rep. of Germany

[73] Assignee: Deutsche Gesellschaft für Wiederaufarbeitung von Kernbrennstoffen mbH, Hanover, Fed. Rep. of Germany

[21] Appl. No.: 169,624

[22] Filed: Mar. 18, 1988

[30] Foreign Application Priority Data

Mar. 18, 1987 [DE] Fed. Rep. of Germany ....... 3708818

[51] Int. Cl.⁴ .............................................. C05B 5/16
[52] U.S. Cl. ......................................... 65/375; 65/260
[58] Field of Search .................. 65/375, 260; 294/106, 294/110.1; 414/160, 209; 266/287

[56] References Cited

U.S. PATENT DOCUMENTS 3,768,853 10/1973 Rennie ............................... 294/110.1

FOREIGN PATENT DOCUMENTS 2911008 9/1980 Fed. Rep. of Germany .

Primary Examiner—David L. Lacey
Assistant Examiner—Joye L. Woodard
Attorney, Agent, or Firm—Walter Ottesen

[57] ABSTRACT

The invention is directed to an apparatus for withdrawing a sample from a glass melting furnace. The apparatus includes a gripper for taking the sample and can be introduced through an opening in the furnace into the interior thereof. The apparatus includes a rectangular vertically upright open guide frame provided with vertical inner guides mounted on the sides of the frame. A carrier frame is mounted on the inner guides and is displaceable relative to the guide frame. The base of the guide frame is penetrated by a guide tube. A pull rod is coaxially and displaceably mounted in the guide tube and is fixedly attached to the base of the carrier frame. Two pairs of articulated lever units for pivoting two cooperating gripper half shells are mounted at the end of the guide tube and at the end of the pull rod. When pivoted together, the gripper half shells conjointly form a closed space to accommodate the sample. The apparatus can be operated from a remote location in a cell of a nuclear facility to obtain representative samples from various regions of the molten glass.

10 Claims, 1 Drawing Sheet

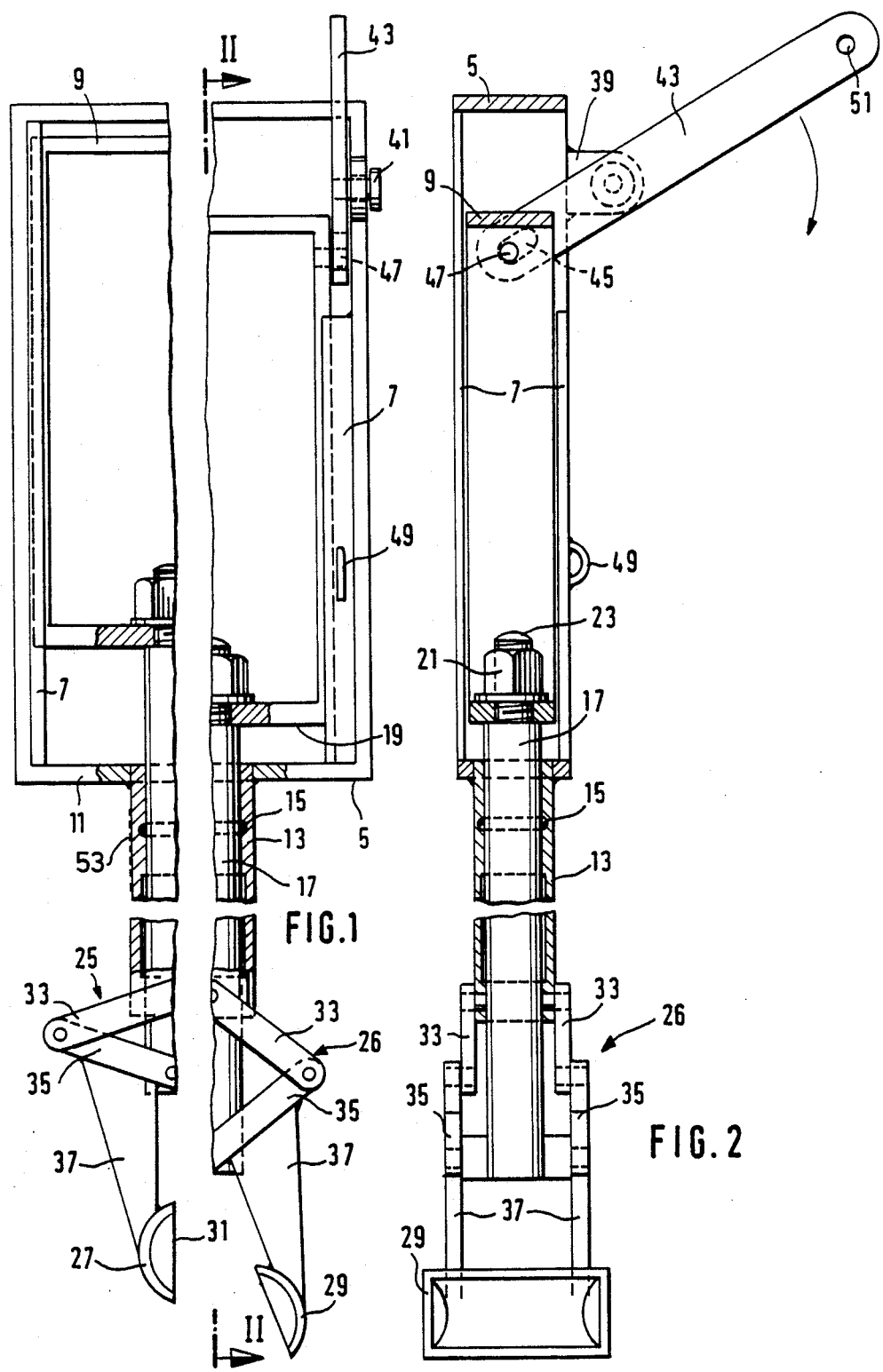

APPARATUS FOR WITHDRAWING A SAMPLE FROM A GLASS MELTING FURNACE

FIELD OF THE INVENTION

The invention relates to an apparatus for withdrawing a sample from a ceramic melting furnace. The apparatus includes a sample gripper movable into the furnace interior through an opening in the latter.

BACKGROUND OF THE INVENTION

The vitrification of highly radioactive waste solutions is carried out in a ceramic melting furnace. It is necessary to take samples from the melting furnace in order to be able to carry out the vitrification process and in order to be able to determine density-related deposits in the molten glass such as metals and rare metals. Previously, glass residues at the base drain of the melting furnace were taken as samples. In this situation, the taking of samples is confined to the area of the outlet orifice. Any deposits which may occur in some other area of the glass melting furnace cannot be examined.

German Pat. No. 2,911,008 discloses a device for taking molten glass from a bath or from a glass melting furnace. The device comprises a rod rotatable about its axis and adapted for insertion into a tap hole provided in the side wall of the glass melting furnace. The rod is rotatable and can be dipped into the molten glass with its free front end. This rod can be removed substantially axially from the side tap hole.

The metals are rinsed off in the molten charge as the device is withdrawn because of the varying density of the molten glass and the heavy and rare metals. Accordingly, it is impossible to obtain a representative sample with this device.

SUMMARY OF THE INVENTION

It is an object of the invention to provide an apparatus of the type described above with which representative samples from various regions of the molten glass can be obtained with remote control under easier and more readily performed remote handling.

The apparatus of the invention can be raised and lowered for withdrawing a sample from a glass-melting furnace having an opening formed therein to facilitate taking a sample of the melt. The apparatus includes an elongated guide frame having a lower base and defining a vertical longitudinal axis; a slider having a lower end and being mounted within the guide frame; guide means in the guide frame for displaceably guiding said slider along the vertical longitudinal axis between upper and lower positions within the guide frame; an annular guide member fixedly mounted in the lower base of the guide frame so as to define a clear passage into the frame, the guide member extending downwardly from the base in the direction of the vertical longitudinal axis so as to be lowerable into the melt through the opening in the furnace; the slider having a pull rod mounted to the lower end of the slider so as to extend coaxially into the passage of the annular guide member and be displaceable relative to the latter as the slider moves between the upper and lower positions; articulated linkage means connected between the lower end of the guide member and the lower end of the pull rod for moving between first and second positions in correspondence with the movement of the slider between the upper and lower positions; and, a pair of grippers mounted on the articulated linkage means for moving between an open position to receive a sample of the melt when the linkage means is in the second position and a closed position when the linkage means is in the first position wherein the grippers conjointly define a closed cavity for holding the sample.

The pair of grippers can be a pair of gripper half shells conjointly forming a closed cavity for holding the sample when in the closed position.

The apparatus according to the invention can be gripped by the slider by means of a crane hook. The dead weight of the other parts of the apparatus acts in the "closure" direction of the apparatus.

The apparatus of the invention is positioned over an opened furnace opening on the top of the glass melting furnace by means of a cell crane. By means of the crane, the apparatus with the grippers closed is lowered so that a portion of the guide member is at a specific depth in the molten glass. The gripper half shells are pivoted apart through a radius and into the open position by a relative downward displacement of the slider in the guide frame. Then the slider is moved upwardly again in the guide frame so that the gripper half shells pivot toward each other to enclose a sample of glass in the sample receiving space which is conjointly defined by the half shells.

The apparatus is pulled upwardly away from the melting furnace and moved away for further handling.

The relative displacement of the guide frame and slider can be performed by the remote handling equipment provided in a shielded cell normally used in a nuclear processing facility because of the simple configuration of the frame and slider.

The relative movement between the guide frame and the slider is converted in a functionally reliable manner into the pivoting movement of the gripper half shells by the articulated linkage connected between the lower end of the guide member and the lower end of the pull rod.

The guide member and the pull rod conjointly define an annular space therebetween and sealing means in the form of a sealing ring is arranged in this annular space. The sealing ring bears tightly on the pull rod in the guide tube. This sealing ring seals the cavity between the guide tube and the pull rod from above in a gas-tight manner. Upon immersion into the molten glass, a cushion of air is created in the guide tube which largely prevents ingress of liquid glass between pull rod and guide tube.

Actuating means in the form of a two-arm lever is mounted on the guide frame for obtaining the relative movement between the guide frame and the slider.

According to another feature of the invention, the parts of the apparatus which come in contact with the molten glass are provided with a coating of graphite. Then after cooling, the glass sample can easily by withdrawn from the gripper half shells. The glass clinging to the rest of the metal can easily be removed so that the remotely-controllable apparatus is quickly ready to be used for taking the next sample of glass.

Pursuant to a further advantageous feature of the invention, the outer surface of the guide tube is provided with a length measuring scale. This visible set of graduations permits an exact positioning of the sample taking apparatus inside the glass melting furnace. Thus, a sample can be withdrawn from any accurately predetermined region of the molten batch.

Latching means are provided on the guide frame for latching the two-arm lever when the same is pivoted to bring the slider into its upper position. The apparatus can be reliably moved out of the molten batch and transported to any desired location without fear of the half shells opening prematurely.

The invention provides an apparatus for taking glass samples which is easily operated by remote control and which, by its ease of remote controllability, permits glass samples to be reliably taken from any desired location in the molten glass.

With the apparatus according to the invention, it is possible to obtain a clearly defined sample which is not mixed. As the gripper half shells are pulled upwardly again, a sample taken from the region close to the bottom of the furnace is reliably enclosed and cannot be mixed with the molten material from other regions of the melt.

BRIEF DESCRIPTION OF THE DRAWINGS

The invention will now be described with reference to the drawings wherein:

FIG. 1 is a front elevation view, partially in section, of an apparatus according to the invention for taking glass samples with the left-hand gripper half shell closed and the right-hand gripper half shell opened; and, FIG. 2 is a side elevation view of the apparatus shown in FIG. 1.

DESCRIPTION OF THE PREFERRED EMBODIMENTS OF THE INVENTION

The remotely controllable apparatus for withdrawing a glass sample shown in FIGS. 1 and 2 comprises a rectangular vertically upright open guide frame 5 which is provided with vertical inner guides 7. A rectangular vertically upright carrier frame 9 is mounted in these inner guides 7 and is displaceable relative to and within the guide frame 5 and is suitable for being held by means of a crane hook.

The base 11 of the guide frame 5 is penetrated centrally by a guide tube 13. An O-shaped sealing ring 15 is seated in the upper part of the guide tube 13. A coaxial pull rod 17 is fixedly attached to the base 19 of the carrier frame 9 and is displaceably mounted in the guide tube 13. The pull rod 17 is attached to base 19 via a threaded stud 23 and a nut 21. Two pairs of articulated lever units (25, 26) are mounted opposite each other at the end of the guide tube 13 and at the end of the pull rod 17. The articulated lever unit pairs (25, 26) support respective gripper half shells (27, 29). The receiving openings of the gripper half shells face towards each other and when they are in the closed position, the gripper half shells (27, 29) conjointly define a space 31 to accommodate the molten glass.

Each pair of articulated lever units (25, 26) has two fixed levers 33 rotatably journalled on the guide tube 13. The free end of each fixed lever 33 is pivotally connected to an end of a carrier lever 35 in such a manner that the lever 33 and lever 35 conjointly define an acute angle. The free ends of the carrier levers 35 are pivotally connected to the end of the pull rod 17 at respective lateral sides thereof as shown in FIG. 2. There is a rigid carrier piece 37 welded to the bottom flank of each carrier lever 35. The two carrier pieces 37 of each pair of articulated lever units (25, 26) carry the corresponding gripper half shell (27 or 29) at the other end thereof.

A bearing block 39 is welded to the side of the upper end of the guide frame 5 and projects forwardly. The bearing block 39 defines a rotary joint 41 for a two-armed actuating lever 43. The shorter end of the actuating lever 43 is provided with a slot 45 which is engaged by a guide bolt 47 mounted laterally on the carrier frame 9.

A latching loop 49 is on the guide frame 5 in the pivoting region of the actuating lever 43 by means of which the latter can be secured in the closed position. One end of a retaining clamp can be hooked into loop 49 while the other end of the clamp engages a bore 51 in lever 43.

The operation of the apparatus of the invention is described below.

The apparatus is picked up on the carrier frame 9 by the hook of a cell crane. While in the closed condition, the apparatus is moved by the cell crane until it is above an open port on the glass melting furnace and is lowered to a predetermined depth into the molten glass. It is advantageous for the upper portion of the guide tube 13 to be provided with a readily visible scale 53 graduated in centimeters. This makes it possible to take a sample from a predetermined region within the melt to an accuracy of within a centimeter.

The hollow space between guide tube 13 and pull rod 17 is sealed in a gas-tight manner by the sealing ring 15 at the upper end of guide tube 13. The air cushion formed in this manner largely prevents the ingress of liquid glass between pull rod 17 and guide tube 13.

The actuating lever 43, which connects the guide frame 5 and carrier frame 9, is now pressed upwardly with a manipulator normally available in nuclear cells. The force is transmitted by the downwardly sliding carrier frame 9 via the pull rod 17 to the pairs of articulated lever units 25 and 26. The gripper half shells 27 and 29 pivot away from each other. Now the actuating lever 43 is pressed downwardly again. The oval gripper half shells 27 and 29 close in that they move towards each other. A sample of the molten material will now be present in the receiving space 31 in the gripper half shells 27 and 29.

The crane is now used to pull the apparatus vertically upwardly out of the glass melting furnace and to bring it into a rest position so that the sample can be cooled. With a manipulator acting on the actuating lever 43 and pressing the latter upwardly, the gripper half shells 27 and 29 are opened again so that the glass sample can be removed. The apparatus which constitutes a glass sample gripper is now ready to be used again to take the next sample.

It is understood that the foregoing description is that of the preferred embodiments of the invention and that various changes and modifications may be made thereto without departing from the spirit and scope of the invention as defined in the appended claims.

What is claimed is:

1. An apparatus which can be raised and lowered for withdrawing a sample from a glass-melting furnace having an opening formed therein to facilitate taking a sample of the melt, the apparatus comprising:

an elongated guide frame having a lower base and defining a vertical longitudinal axis;

a slider having a lower end and being mounted within said guide frame;

guide means in said guide frame for displaceably guiding said slider along said axis between upper and lower positions within said guide frame;

an annular guide member fixedly mounted in said base so as to define a clear passage into said frame, said guide member extending downwardly from said base in the direction of said axis so as to be lowerable into the melt through the opening in the furnace;

said slider having a pull rod mounted to said lower end of said slider so as to extend coaxially into said passage of said annular guide member and be displaceable relative to the latter as said slider moves between said upper and lower positions;

articulated linkage means interconnecting the lower end of said guide member and the lower end of said pull rod for moving between first and second positions in correspondence with the movement of said slider between said upper and lower positions; and, a pair of grippers mounted on said articulated linkage means for moving between an open position to receive a sample of the melt when said linkage means is in said second position and a closed position when said linkage means is in said first position wherein said grippers conjointly define a closed cavity for holding the sample.

2. The apparatus of claim 1, said pair of grippers comprising a pair of gripper half shells conjointly forming a closed cavity for holding the sample when in said closed position.

3. The apparatus of claim 2, said articulated linkage means comprising:

two sets of lever arm pairs arranged on respective diametrically opposite sides of said annular guide member and said pull rod;

each one of said sets of lever arm pairs having a right-hand lever arm pair and a left-hand lever arm pair; each of said lever arm pairs including: a first lever arm with one end thereof pivotally connected to said annular guide member; a second lever arm with one end thereof pivotally connected to said pull rod; and, said first and second levers being pivotally connected to each other at their respective other ends so as to conjointly define an acute angle which becomes smaller and larger as said slider moves between said upper and lower positions;

each of said second levers having a downwardly facing flank and a carrier piece rigidly connected to said flank; and, one of said gripper half shells being attached to the two carrier pieces of the right-hand lever arm pairs of said sets and the other one of said gripper half shells being attached to the two carrier pieces of the left-hand lever arm pairs of said sets.

4. The apparatus of claim 1, said guide member and said pull rod conjointly defining an annular space therebetween; said apparatus comprising sealing means arranged in said annular space to maintain an air cushion in said annular space to prevent molten glass from entering said space when a sample is taken from the melt.

5. The apparatus of claim 4, said sealing means comprising a groove formed in the inner wall of said guide member; and, a sealing ring seated in said groove so as to be in sealing contact engagement with the surface of said pull rod.

6. The apparatus of claim 1, comprising actuating means mounted on said guide frame for moving said slider between said upper and lower positions.

7. The apparatus of claim 6, said actuating means comprising a two-arm lever pivotally mounted on said guide frame; a stud formed on said slider; and, one of the arms of said two-arm lever having a slot formed therein for engaging said stud for moving said slider between said upper and lower positions when said lever is pivotally actuated.

8. The apparatus of claim 7, comprising latching means on said guide frame for latching said two-arm lever when the same is pivoted to bring said slider into said upper position.

9. The apparatus of claim 1, said annular guide member, said pull rod, said articulated linkage means and said grippers all being coated with graphite.

10. The apparatus of claim 1, comprising scale means formed on the outer surface of said annular guide member to provide a visual indication of the depth to which said guide rod is dipped into the melt when taking a sample.

* * * * *